United States Patent [19]
Girvin et al.

[11] Patent Number: 5,864,399
[45] Date of Patent: *Jan. 26, 1999

[54] METHOD FOR COUNTING PARTICLES IN A FLUENT STREAM

[75] Inventors: Kenneth L. Girvin, Grants Pass; Richard K. DeFreez, Hillsboro, both of Oreg.

[73] Assignee: Met One, Inc., Grants Pass, Oreg.

[*] Notice: The term of this patent shall not extend beyond the expiration date of Pat. No. 5,642,193.

[21] Appl. No.: 879,665

[22] Filed: Jun. 23, 1997

Related U.S. Application Data

[63] Continuation of Ser. No. 614,814, Mar. 8, 1996, Pat. No. 5,642,193.
[51] Int. Cl.$^6$ .................................................... G01N 15/06
[52] U.S. Cl. ............................................................ 356/339
[58] Field of Search ...................................... 356/338, 339

[56] References Cited

U.S. PATENT DOCUMENTS

| | | | |
|---|---|---|---|
| 4,571,079 | 2/1986 | Knollenberg | 356/336 |
| 4,594,715 | 6/1986 | Knollenberg | 372/32 |
| 4,685,802 | 8/1987 | Saito et al. | 356/339 |
| 4,746,215 | 5/1988 | Gross | 356/339 |
| 4,798,465 | 1/1989 | Knollenberg | 356/336 |
| 5,033,851 | 7/1991 | Sommer | 356/338 |
| 5,061,065 | 10/1991 | Sommer | 356/338 |
| 5,084,879 | 1/1992 | Suzuki et al. | 372/22 |
| 5,085,500 | 2/1992 | Blesener | 356/338 |
| 5,092,675 | 3/1992 | Sommer | 356/338 |
| 5,121,988 | 6/1992 | Blesener et al. | 356/442 |
| 5,135,304 | 8/1992 | Miles et al. | 356/301 |
| 5,191,588 | 3/1993 | Dacquay | 372/22 |
| 5,317,447 | 5/1994 | Baird et al. | 359/328 |
| 5,483,546 | 1/1996 | Johnson et al. | 372/10 |
| 5,642,193 | 6/1997 | Girvin et al. | 356/339 |
| 5,726,753 | 3/1998 | Sandberg | 356/338 |

FOREIGN PATENT DOCUMENTS 61-243345   10/1986   Japan ...................................... 356/339

OTHER PUBLICATIONS

Burton G. Schuster et al., "Detection and Sizing of Small Particles in an Open Cavity Gas Laser", *Applied Optics*, vol. 11, No. 7, pp. 1515–1520 (Jul.1972).

Robert G. Knollenberg et al., "Open Cavity Laser 'Active' Scattering Particle Spectrometry from 0.05 to 5 Microns", *Fine Particles—Aerosol Generation, Measurement, Sampling, and Analysis*, Academic Press, pp. 669–696 (May 1975).

*Primary Examiner*—Richard A. Rosenberger
*Attorney, Agent, or Firm*—Thomas Schneck; John P. McGuire, Jr.

[57] ABSTRACT

A particle detector employs a laser having a solid-state lasing medium, such as an Nd:YAG crystal, disposed in a resonant cavity, and includes an intracavity view volume. The resonant cavity is defined by two spaced apart mirrors, with the laser medium positioned between them, defining a light path. A pump source is optically coupled to drive the laser medium to produce coherent light having a first wavelength. The view volume is positioned in the light path, between the first mirror and the laser medium, to introduce particles into the resonant cavity so that light impinging there-upon produces scattered light. A detector is disposed to sense light scattered from the view volume and produces signals proportional to the light sensed. A displaying device, such as a pulse height analyzer, is in electrical communication to receive the signals produced by the detector to quantitatively display the intensity of the light sensed. In an alternate embodiment, a harmonic generator is disposed within the light path to shorten the wavelength of light impinging upon particles in the view volume, making the detector more sensitive to particles of sub-micron size.

6 Claims, 3 Drawing Sheets

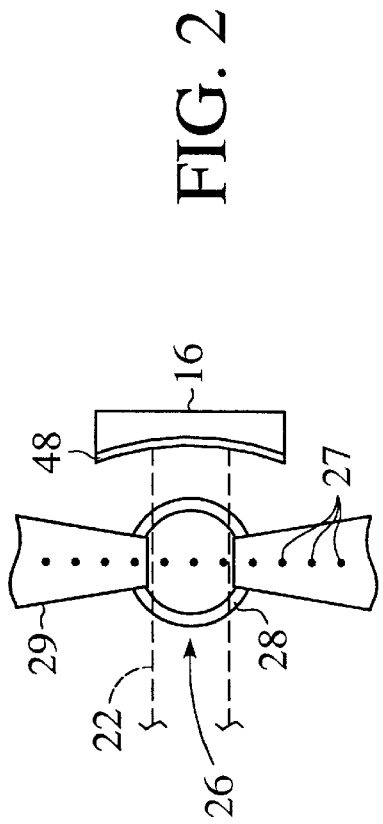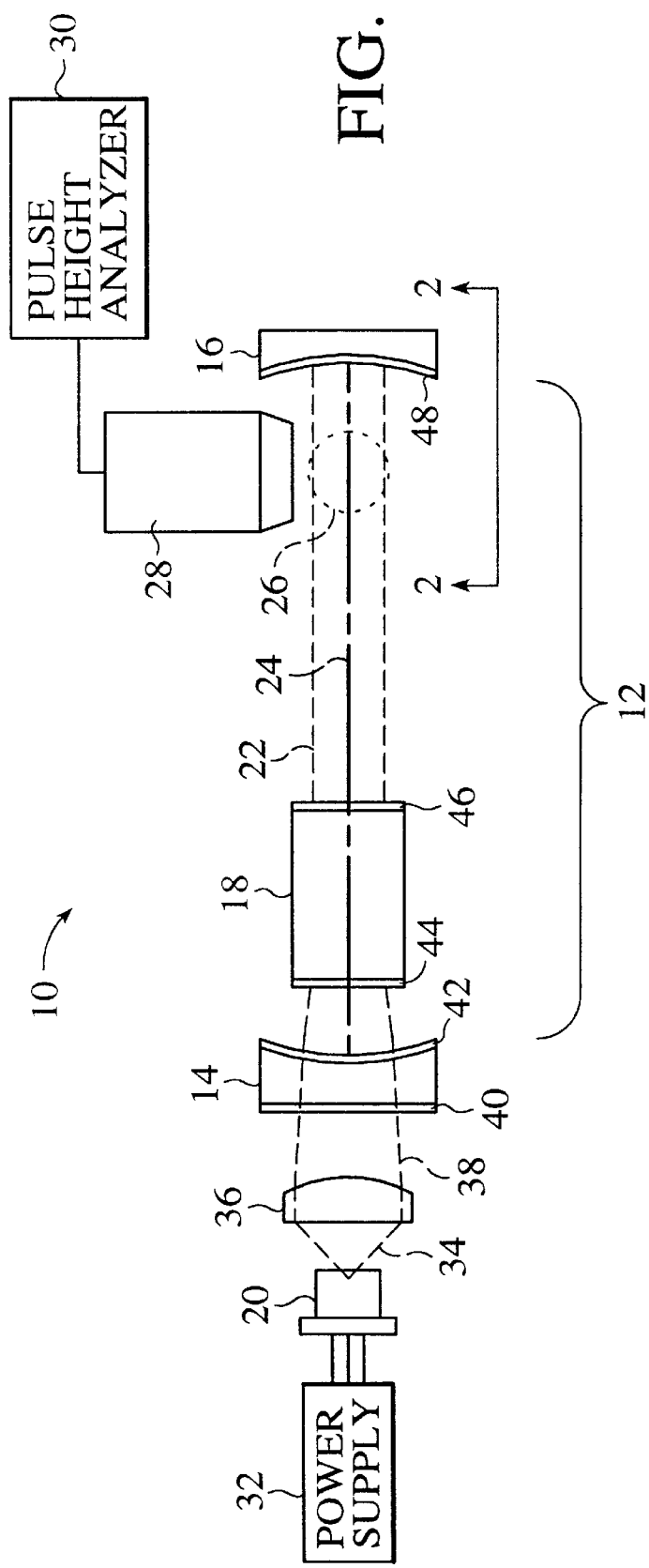

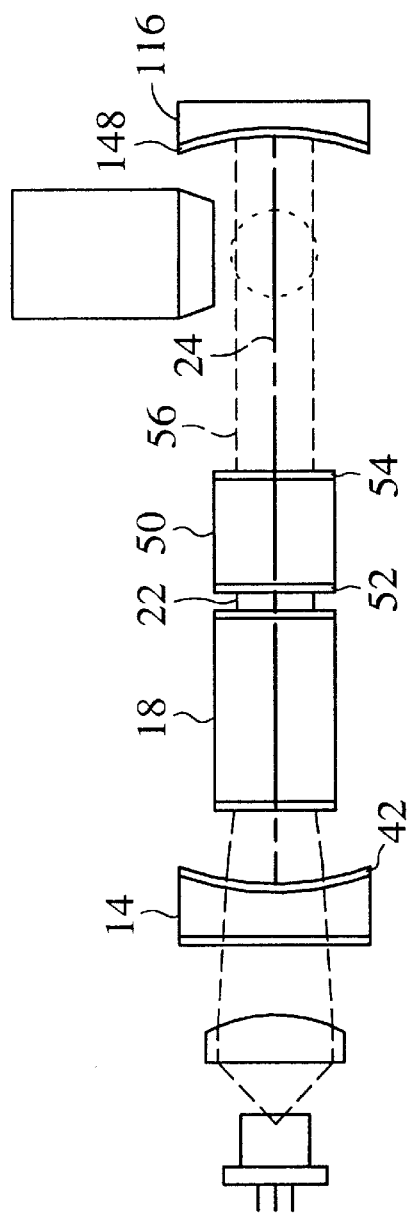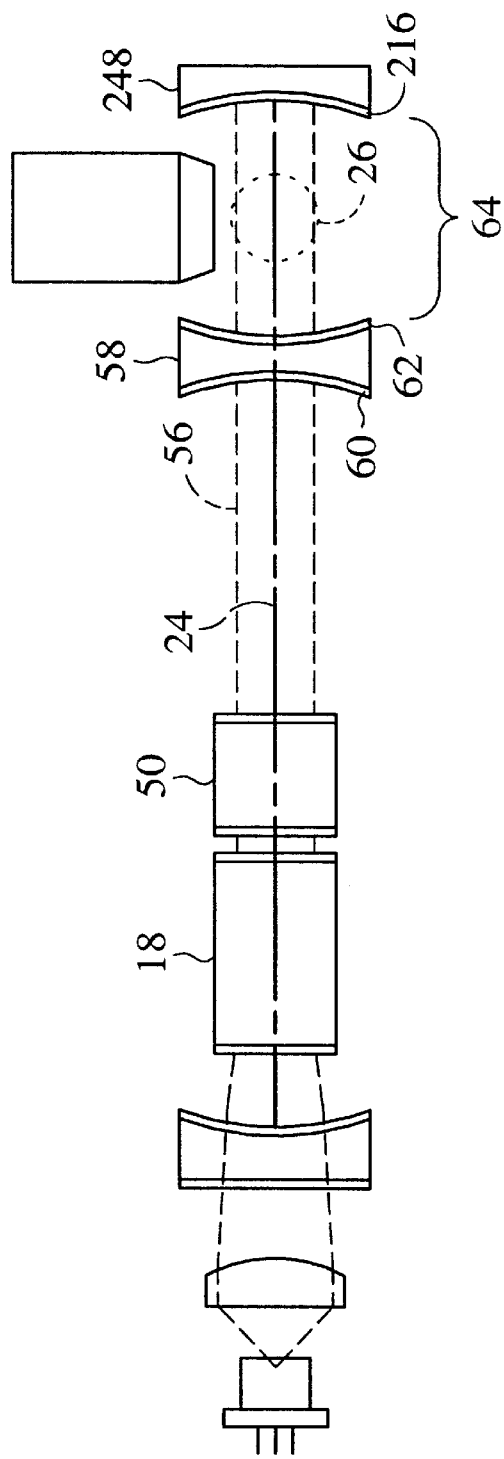

5,864,399

METHOD FOR COUNTING PARTICLES IN A FLUENT STREAM

This is a continuation of application Ser. No. 08/614,814 filed on Mar. 8, 1996, now U.S. Pat. No. 5,642,193.

TECHNICAL FIELD

The present invention pertains to the field of particle counters. Specifically, the present invention pertains to a method for counting particles in a fluid stream.

BACKGROUND ART

Typically, particle detectors employ laser devices producing a beam of coherent light that is directed to impinge upon a sample of particles. Particle detection is achieved either by sensing light scattered by a particle, e.g. U.S. Pat. No. 5,085,500 to Blesener et al., or by detecting extinction of light, e.g. U.S. Pat. No. 5,121,988 to Blesener et al. U.S. Pat. No. 5,317,447 to Baird et al. discloses, in pertinent part, a solid-state laser having a Cr:LiCAlF crystal pumped from one end by an array of tunable semiconductor laser diodes. Tilted birefringent plates are positioned within the solid-state resonator cavity to control the spectral bandwidth and wavelength output. A periodically segmented domain-inverted KTP waveguide is disposed outside of the resonant cavity, in the path of the output beam, to shorten the wavelength of the beam passing there-through. Despite the recent advances in solid-state laser technology, it has not been applied to particle detectors.

Particle detectors have been used for a variety of purposes to detect the presence and/or size of particles in various fluids, including air and other gases, as well as liquids, such as water, hydraulic oils and lubricants. They have proved particularly useful to control contamination in many industrial environments. For example, particulate contamination can cause hydraulic equipment and the like to fail due to excessive accumulation of particles in the hydraulic fluid. Even though filters are used in such equipment to continuously remove particles, the filters may become clogged and may rupture due to excess pressure build-up across the filter membrane. Also, microelectronic fabrication requires a "clean room" in which particulate contaminants, e.g., dust, are filtered from an atmosphere of a room. The filters used in "clean rooms" are also subject to clogging and compromise, resulting in particulate matter entering a "clean room" atmosphere in great quantities. Failure to provide a "clean room" results in particulate contamination of the devices during fabrication, which reduces yield. Particle detectors are thus used in such environments to detect particles in specified size classes and report the cleanliness level of the fluid according to categories specified by industry standards.

A significant amount of research has been performed using open cavity gas lasers in particle detection systems and is discussed by R. G. Knollenberg and B. Schuster in "Detection and Sizing of Small Particles in an Open Cavity Gas Laser", Applied optics, Volume 11, Number 7, November 1972, pages 1515–1520. Sub-micron particle sizing devices utilizing light scattering in an open cavity laser device is described by R. G. Knollenberg and R. E. Leur in "Open Cavity Laser 'Active' Scattering Particle Spectrometry from 0.05 to 5 Microns", Fine Particles, Aerosol, Generation Measurement, Sampling and Analysis, Editor Benjamin Y.H. Liu, Academic Press, May, 1975, pages 669,696. However, the susceptibility of the open cavity gas lasers to contamination has made them require more frequent servicing to clean the laser optics, leading to the development of the external cavity gas laser.

U.S. Pat. No. 4,594,715 to Knollenberg discloses an external cavity gas laser for use as a particle detector that includes first, second and third spaced mirrors. The first and second mirrors define an active resonant cavity of a gas laser, and the second and third mirrors define a second cavity. The second cavity ranges between being passive and being closely coupled as part of the active cavity, depending on the phase of the light returned from the third mirror to the second mirror. In the limiting case where the second cavity is not resonant, a large field does not build up in the passive cavity, because that cavity is off resonance for the wavelength of the active cavity. In the latter case, the second mirror, ignoring scattering and absorption losses in its coating and substrate, becomes transparent to light recirculating in the external cavity formed by the first and third mirrors, thus destabilizing the original cavity modes of the resonator formed by the first and second mirrors. In this case, even a small amount of absorption or scattering in the coating or substrate of the second mirror will result in the resonator formed by the first and third mirrors to have low net gain. This is because the inherent low gain of many types of gas lasers renders them particularly sensitive to intracavity loss. To address these issues, Knollenberg describes a method to modulate the external cavity along the laser axis, thereby creating a broad, Doppler induced, incoherent spectrum. This reduces the Q value of that cavity, because the nominal Q, as calculated from standard Fabry-Perot formulas, depends, for buildup of optical power, on having a resonance wavelength as opposed to a broad spectrum.

It is an object, therefore, of the present invention to provide a particle detector having increased sensitivity to detecting aerosol particles of sub-micron size.

It is a further object of the present invention to provide a laser source for a particle detector that is less sensitive to optical loss caused by detection of aerosol particulates.

SUMMARY OF THE INVENTION

These objects have been achieved by providing a solid-state lasing medium, such as an Nd:YAG crystal, disposed in a resonant cavity that includes an intracavity view volume. The resonant cavity is defined by two spaced apart mirrors, with the lasing medium positioned between them, defining a light path. A pump source is optically coupled to drive the laser medium to produce coherent light having a first wavelength. The view volume is positioned in the beam path, between the first mirror and the lasing medium, to introduce particles into the resonant cavity so that light impinging thereupon produces scattered light. A detector is disposed to sense light scattered from the view volume and produces signals proportional to the light sensed. A displaying device, such as a pulse height analyzer, is in electrical communication to receive the signals produced by the detector to quantitatively display the intensity of the light sensed. In an alternate embodiment, a harmonic generator is disposed within the resonant cavity. The harmonic generator is disposed between the lasing medium and the view volume and shortens the wavelength of the light produced by the lasing medium that passes therethrough.

In another embodiment, the view volume is disposed in a second separate cavity unidirectionally optically coupled to the resonant cavity. A harmonic generator is disposed in the resonant cavity to produce light having a second wavelength by shortening the wavelength of the light produced by the lasing medium. One of the mirrors forming the resonant cavity functions as a wavelength separator by reflecting light at the lasing wavelength while being transmissive with respect to light at the second wavelength. In this fashion, the second cavity includes light having only the second wavelength.

In still another embodiment, three cavities are formed. The resonant cavity is optically coupled to a second cavity as described above. Disposed in the second cavity, however, is a second harmonic generator to produce light having a third wavelength by shortening light having the second wavelength. The second cavity is unidirectionally optically coupled to a third separate cavity, where the view volume is disposed. A second wavelength separator partitions the second and third cavity. The second wavelength separator is a mirror reflecting light having the second wavelength while being transmissive to light having the third wavelength. In this fashion, the third cavity includes light having only the third wavelength.

BRIEF DESCRIPTION OF THE DRAWINGS

FIG. 1 shows a simplified plan view of the present invention.

FIG. 2 shows a partial cross-sectional view of the view volume shown in FIG. 1 taken across lines 2—2.

FIG. 3 shows a simplified plan view of the present invention in accord with a first alternate embodiment.

FIG. 4 shows a simplified plan view of the present invention in accord with a second alternate embodiment.

BEST MODE FOR CARRYING OUT THE INVENTION

Figure 5:
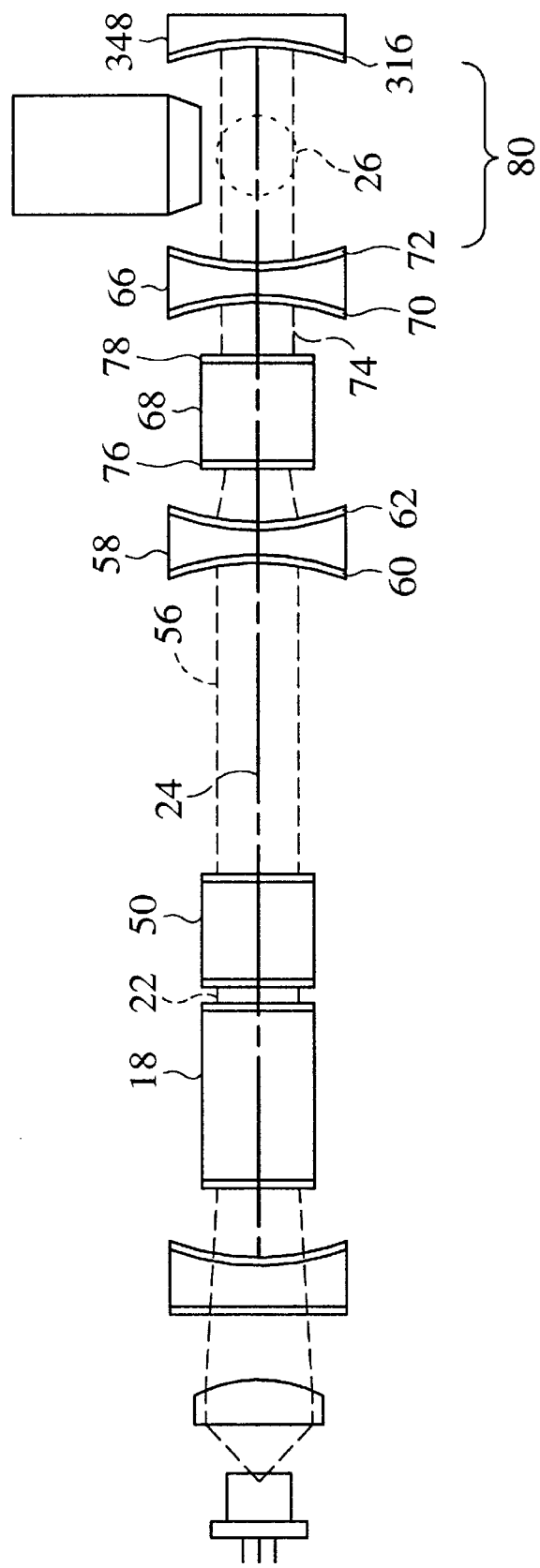
FIG. 5 shows a simplified plan view of the present invention in accord with a third alternate embodiment.

FIG. 1 shows a particle detector 10 in accord with the present invention, including a resonant cavity 12 defined by two spaced apart mirrors 14 and 16. A lasing medium 18 is positioned within the resonant cavity 12, between mirrors 14 and 16. A pump source 20 is optically coupled to drive the lasing medium 18 to produce coherent light 22 that propagates along a beam path 24, defined by the lasing medium 18. A view volume 26, defined by injector ports (not shown), is positioned in beam path 24 between mirror 16 and lasing medium 18. The injector ports introduce particles into view volume 26 so that light impinging upon particles in view volume 26 produces scattered light. A detector 28 is disposed to sense light scattered from view volume 26 and produces signals proportional to the light sensed. Typically, the detector is positioned to sense light scattered in a direction substantially perpendicular to both light path 24 and the longitudinal axis of view volume 26. A displaying device 30, such as a pulse height analyzer, is in electrical communication to receive the signals produced by detector 28 to quantitatively display the intensity of the light sensed.

Although any lasing medium may be employed, preferably lasing medium 18 has a crystalline structure that has been embedded with a light emitting species, for example Nd:YAG, Nd:YLF or Cr:LiCAF. The pump source desired is dependent upon the lasing medium employed. Preferably, an optical pump source is employed that is capable of emitting light having a wavelength matching the absorption wavelength of the light emitting species in lasing medium 18. It is preferred, however, that pump source 20 is a semiconductor laser diode in electrical communication with a power supply 32 to supply the requisite current to produce coherent light 34. Beam shaping optics 36 are disposed in the path of coherent light 34, between mirror 14 and pump source 20, to produce a pump beam 38. Mirror 14 is transmissive with respect to the wavelength of pump beam 38, but preferably has an anti-reflective coating 40 disposed on a surface facing optics 36 to suppress reflection of the same. Preferably, coating 40 suppresses reflection of light having a wavelength approximating the absorption wavelength of lasing medium 18. A dichroic coating 42 is disposed on a surface of mirror 14, opposing coating 40. Coating 42 exhibits the same properties as coating 40, with respect to beam 38. In this fashion, coatings 40 and 42 provide mirror 14 with highly transmissive surfaces through which a maximum intensity of pump beam 38 may pass.

In addition, an end of medium 18 facing mirror 14 includes a coating 44 which suppresses reflection of light having a wavelength approximating the emission wavelength, as well as light having a wavelength approximating the absorption wavelength of lasing medium 18. An end of medium 18, in opposing relation to coating 44, includes a coating 46 which also suppresses reflection of light having a wavelength approximating the emission wavelength. In this fashion, coatings 44 and 46 provide a highly transmissive surface through which a maximum intensity of beam 22 may pass.

The opposed ends of resonant cavity 12 is formed by coating 42 and coating 48, with coating 48 being disposed on mirror 16. Coatings 42 and 48 both provide optical properties to reflect all light having a wavelength approximating the wavelength of the light produced by lasing medium 18. In this manner, beam 22's egression from resonant cavity 12 is completely blocked, thereby unidirectionally coupling cavity 12 with the pump source.

Referring also to FIG. 2, particles 27 are introduced into view volume 26 via injector ports 29 so that light impinges on them. The particles scatter light, and a photo-detector 28, in optical communication with view volume 26, detects the scattered light. Detector 28 produces signals proportional to the light sensed. Pulse height analyzer 30 receives the signals and quantitatively displays the intensity of the light sensed. Negligible cavity losses result from the scattering of light by the particles due to their small size.

An advantage with preventing light 22 from exiting resonant cavity 12 is that this provides a greater amount of optical energy to produce lasing action in lasing medium 18. This makes the particle detector less sensitive to optical loss caused from the scattering of light by particles present in view volume 26. This structure augments the inherent insensitivity of a solid-state laser to optical loss typically caused by intracavity optical surfaces, resulting in an improved signal-to-noise ratio for detecting particles of sub-micron size.

The amount of light scattered from a particle having a diameter less than the wavelength of light impinging upon it is defined as follows:

$$D^6/\lambda^4$$

where D is the particle diameter and $\lambda$ is the wavelength of the scattered light. Therefore, to increase the amount of light scattered for a particle of a given size, it is desirable to decrease the wavelength $\lambda$ of the light impinging thereupon. This is particularly useful to increase the resolution of the particle detector by making it more sensitive to particles of very small size. Decreasing the wavelength of light also facilitates characterizing the morphology of larger particles.

FIG. 3 shows an alternate embodiment of the present invention taking advantage of the aforementioned concepts.

To shorten the wavelength of the light 22 emitted from lasing medium 18, a crystal harmonic generator 50 is disposed in light path 24, between mirror 116 and lasing medium 18. Dichroic coating 52 and coating 54 are present on opposite ends of the harmonic generator 50, providing highly transmissive surfaces through which light 22 may pass, as discussed above with respect to coatings 44 and 46. Typically, the crystal harmonic generator 50 is a frequency doubling crystal that shortens the wavelength of light 22 by 50%, producing light 56. Coating 52 also includes optical properties to reflect all light having a wavelength approximating 50% of the lasing wavelength. This effectively optically decouples light 56 from lasing medium 18 by preventing light 56 from passing through the same. In addition, coating 54 has optical properties to suppress reflectivity of light having a wavelength approximating 50% of the lasing wavelength. A coating 148 is disposed on mirror 116 having optical properties to reflect light having the wavelengths associated with beam 22 and light 56. In this fashion, light 56 is reflected between coatings 52 and 148. This increases the effective length of crystal generator 50, which establishes a mode to maximize the optical energy from the same.

FIG. 4 is an alternate embodiment of the invention shown in FIG. 3 wherein a third mirror 58, having opposed major surfaces, is disposed between view volume 26 and harmonic generator 50. Third mirror 58 functions as a wavelength separator. To that end, the opposed surfaces of mirror 58 are coated with an anti-reflective coatings 60 which suppresses reflectivity of light having a wavelength approximating 50% of the lasing wavelength. Dichroic coating 60 also reflects light having a wavelength approximating the lasing wavelength of the light produced by the lasing medium 18. The surface of mirror 248, facing mirror 58, includes a coating 216 which is highly reflective to light approximating 50% of the lasing wavelength. In this fashion, a second cavity 64 is defined between mirrors 58 and 248, which is optically coupled to the remaining cavities in a unidirectional manner so that only light having a wavelength approximating 50% of the wavelength of the light produced by the lasing medium 18 is present therein. Thus, second cavity 64 allows detection of particles having a very small size, for the reasons discussed above with respect to FIGS. 1 and 2.

To further enhance the performance of the detector, an active length stabilization system may be employed. This would allow stabilization of the length of external cavities, such as cavity 64, to simultaneously promote high circulating power, while minimizing transmission of light therefrom. In addition, mode matching optics, such as lenses, may be disposed to optically couple cavity 64 with the active cavity.

FIG. 5 shows a third alternate embodiment of the invention substantially similar to the embodiment shown in FIG. 4 with the addition of a fourth mirror 66 and a second harmonic generator 68, both of which are disposed in beam path 24. Fourth mirror 66 is disposed between view volume 26 and third mirror 58. Generator 68 is disposed between third 58 and fourth 66 mirrors to shorten the wavelength of the light emitted from harmonic generator 50. In this fashion, light 74, having a wavelength approximating 25% of the lasing wavelength, is produced. On a surface of generator 68, facing mirror 58, is a dichroic coating 76. Coating 76 is highly reflective to light 74 and suppresses reflection of light 56, effectively optically decoupling light 74 from generator 50 and medium 18 to provide the benefits discussed above with respect to FIG. 3.

On a surface of generator 68, opposing coating 76, is a coating 78 which suppresses reflection of light 56 and 74. A dichroic coating 70 is disposed on the surface of mirror 66, facing generator 68. Coating 70 is highly reflective to light 56 and suppresses the reflection of light 74. Having light 54 reflected back into generator 68 by coating 70 establishes a mode to maximize the optical energy from generator 68. On the surface of mirror 66, opposing coating 70, is a coating 72 that also suppresses reflection of light 74. In this fashion, coatings 70 and 72 provide mirror 66 with two highly transmissive surfaces through which light 74 may propagate. A coating 316 is disposed on a surface of mirror 348, facing coating 72. Coating 316 is highly reflective of light having a wavelength 25% of the lasing wavelength. Coatings 76 and 70 function to increase the effective length of second harmonic generator 68. Mirror 66 and 348 define a third cavity 80 coupled to the remaining cavities of the system so that only light having a wavelength 25% of the lasing wavelength is present therein. In this fashion, third cavity 80 allows detection of particles on the order of .04 micron, for the reasons discussed above with respect to the second cavity shown in FIGS. 1 and 2.

The comparative wavelengths obtained using the aforementioned particle detectors is as follows:

| Lasing Medium | Embodiment | Characteristic Wavelength ($\mu$m) In the View Volume |
|---|---|---|
| Nd:YAG | FIG. 1 | 1.064 |
| Nd:YAG | FIG. 4 | 0.532 |
| Nd:YAG | FIG. 5 | 0.266 |
| Nd:YLF | FIG. 1 | 1.047 |
| Nd:YLF | FIG. 4 | 0.524 |
| Nd:YLF | FIG. 5 | 0.262 |
| Cr:LiCAF | FIG. 1 | 0.770 |
| Cr:LiCAF | FIG. 4 | 0.385 |

Ignoring relative photo-detector spectral response and for equal intensity illuminating the particle, the diameter of the particle that can be detected using shorter wavelength radiation expressed in terms of the diameter that can be detected using longer wavelength radiation is given by:

$$D_{short\lambda} = \left( \frac{\lambda_{short}}{\lambda_{long}} \right)^{2/3} D_{long\lambda}$$

where $\lambda_{short}$ is the short wavelength of light compared to $\lambda_{long}$, $D_{short\lambda}$ is the diameter of a particle measured using the short wavelength of light, and $D_{long\lambda}$ is the diameter of a particle measured using the long wavelength of light. The Nd:YLF lasing medium and a quadrupled wavelength from a fourth harmonic generator crystal will produce a wavelength of 262 nm. The HeNe laser wavelength is 632.8 nm. In the above equation, the sensitivity gained from the difference in wavelength alone would allow one to see 0.055 $\mu$m particles instead of 0.1 $\mu$m particles.

We claim:

1. A method of counting particles in a fluent medium comprising, providing a laser cavity between first and second spaced apart mirrors with a lasing crystal therein, the mirrors being highly reflective to laser light and confining substantially all laser light therebetween, exciting laser action in said lasing crystal using a semiconductor diode laser stimulating the lasing crystal to produce laser light, providing a harmonic generator in said laser cavity, together with a wavelength-selection means associated therewith, for introducing light into said cavity having a predetermined wavelength, infecting a fluent medium having particles suspended therein through ports into a view volume, placing the view volume inside of the laser cavity in the light path of light from the laser crystal, detecting light scattered from particles in the view volume and producing electrical signals in response, and counting particles based upon said electrical signals.

2. A method of counting particles in a fluent medium comprising, providing a first laser cavity between first and second spaced apart highly reflective mirrors with a lasing crystal therein, the mirrors confining substantially all laser light and harmonic wavelength therebetween, exciting laser action in said laser crystal using a semiconductor diode laser stimulating the lasing crystal to produce laser light, providing a harmonic generator to produce a harmonic wavelength of the lasing wavelength in the laser cavity, providing a view volume between said first and second mirror, injecting a fluent medium having particles suspended therein through ports into said view volume, detecting light scattered from particles in said view volume and producing electrical signals in response, and counting particles based upon said electrical signals.

3. A method of counting particles in a fluent medium comprising, providing a first laser cavity between first and second spaced apart mirrors, with a lasing crystal therein, the mirrors being highly reflective to laser light, exciting laser action in said laser crystal using a semiconductor diode laser stimulating the lasing crystal to produce laser light, providing a third mirror, spaced apart from the second mirror, establishing a second cavity, the second mirror allowing optical communication between the second and first resonant cavities, the third mirror being highly reflective to laser light, the first, second and third mirrors confining substantially all laser light between the first and third mirrors, providing a harmonic generator in a selected one of said first and second cavities, together with a wavelength selection means, associated with said harmonic generator, for introducing light into said selected cavity having a predetermined wavelength and obstructing light having a wavelength differing from said predetermined wavelength, injecting a fluent medium having particles suspended therein through ports into a view volume, placing the view volume inside of the second laser cavity in the light path of light from the laser crystal, detecting light scattered from particles in the view volume and producing electrical signals in response, and counting particles based upon said electrical signals.

4. The method of claim 3 further defined by selecting said crystal and said harmonic generator to produce light in the range of 0.385 to 0.532 micrometers in wavelengths.

5. A method of counting particles in a fluent medium comprising, providing a first laser cavity between first and second spaced apart mirrors, with a lasing crystal therein, providing a third mirror spaced apart from the second mirror defining a second cavity in optical communication with the first cavity, providing a fourth mirror spaced apart from the third mirror defining a third cavity in optical communication with both the first cavity and the second cavity, the first, second, third and fourth mirrors being highly reflective to laser light and confining substantially all laser light between the first and fourth mirrors, providing at least one harmonic generator in a selected one of said first, second and third cavities, together with a wavelength selection means, associated with said harmonic generator, for introducing light having a predetermined wavelength and obstructing light having a wavelength differing from said predetermined wavelength, injecting a fluent medium having particles suspended therein through ports into a view volume, placing the view volume inside of the third cavity in the light path of the light from the laser crystal, detecting light scattered from particles in the view volume and producing electrical signals in response, and counting the particles based upon said electrical signals.

6. The method of claim 5 further defined by selecting said crystal and said harmonic generator to produce light in the range of 0.192 to 0.266 micrometers in wavelength.

* * * * *